United States Patent [19]
Altshuler et al.

[11] Patent Number: 6,015,404
[45] Date of Patent: *Jan. 18, 2000

[54] LASER DERMATOLOGY WITH FEEDBACK CONTROL

[75] Inventors: Gregory Altshuler, Beverly, Mass.; Andrei V. Erofeev, St. Petersburg, Russian Federation

[73] Assignee: Palomar Medical Technologies, Inc., Burlington, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/759,036

[22] Filed: Dec. 2, 1996

[51] Int. Cl.$^7$ ........................................ A61N 5/06
[52] U.S. Cl. .................................. 606/9; 606/10
[58] Field of Search ................... 606/2, 3, 4, 5, 606/6, 10, 11, 12, 14, 15, 16, 17, 19

[56] References Cited

U.S. PATENT DOCUMENTS

| | | | |
|---|---|---|---|
| 5,057,104 | 10/1991 | Chess | 606/9 |
| 5,071,417 | 12/1991 | Sinofsky | 606/8 |
| 5,137,530 | 8/1992 | Sand | 606/5 |
| 5,140,984 | 8/1992 | Dew et al. | 606/2 X |
| 5,207,671 | 5/1993 | Franken et al. | 606/9 |
| 5,334,191 | 8/1994 | Poppas et al. | 606/12 |
| 5,334,193 | 8/1994 | Nardella | 606/41 |
| 5,344,418 | 9/1994 | Ghaffari | 609/9 |
| 5,348,551 | 9/1994 | Spears et al. | 606/5 |
| 5,350,376 | 9/1994 | Brown | 606/12 |
| 5,415,654 | 5/1995 | Daikuzono | 606/13 |
| 5,782,249 | 7/1998 | Weber et al. | 606/16 |

FOREIGN PATENT DOCUMENTS

| | | |
|---|---|---|
| 0 755 698 A2 | 1/1997 | European Pat. Off. . |
| 38 37 248 | 3/1990 | Germany . |
| WO 96/25979 | 8/1996 | WIPO . |

OTHER PUBLICATIONS

Belikov, A. V., A. G. Novikov and A. V. Scrypnik, "Identification of enamel and dentine under tooth laser treatment" *SPIE*, 2623:109–116, 1995.

Altshuler, G. B, et al., "Acoustic response of hard dental tissues to pulsed laser action." *SPIE*, 2080:97–103, 1993.

*Primary Examiner*—Robert L. Nasser
*Attorney, Agent, or Firm*—Wolf, Greenfield & Sacks, P.C.

[57] ABSTRACT

Method and apparatus are provided for use with systems applying laser energy to treat a selected dermatology problem. The method and apparatus protect skin not under treatment in skin regions affected by the laser by detecting, with a suitable sensor, at least a selected parameter in the skin region affected by the delivered laser energy and performing a control function to effect the desired protection by use of a feedback mechanism which is operative in response to an output from the sensor. For some embodiments, two laser pulses may be utilized, which pulses are spaced by a time which is preferably greater than the thermal relaxation time for affected regions not under treatment, for example an epidermis through which the energy is passed to an area under treatment, but is less than the thermal relaxation time of the area under treatment. The first of the pulses serves as a prediagnosis pulse which is clearly below the damage threshold for protected areas, with the sensor output for the first pulse being utilized to control at least one parameter of the second pulse.

9 Claims, 4 Drawing Sheets

LASER DERMATOLOGY WITH FEEDBACK CONTROL

FIELD OF THE INVENTION

This invention relates to the field of laser dermatology and more particularly to a laser dermatology system which minimizes epidermal damage by detecting a selected epidermal condition and utilizing the detected epidermal condition to control selected system parameters.

BACKGROUND OF THE INVENTION

Lasers are being increasingly utilized to treat various dermatological conditions, and in particular to treat and destroy in various ways hair follicles for the removal of unwanted hair, spider veins, leg veins, other veins or blood vessels in the upper portions of the dermis which are visible through the epidermis, lesions, unwanted tattoos and the like. One problem with such laser treatments is that the only way to get the laser energy to the area in the dermis where treatment is desired is to transmit the laser energy to such area through the overlying epidermis. Further, since many of the treatments involve absorption of energy by the melanin in the dermal area being treated, and there is also melanin in the epidermis, particularly in the inner portion thereof, it is not possible to use a wavelength of laser energy for the treatment which will not also be absorbed to some extent in the epidermis. Even when wavelengths are used which are preferentially absorbed by blood or hemoglobin, there is still some absorption of laser energy in the epidermis. Further, the deeper in the dermis that treatment is desired and/or the larger the element being treated, the more laser energy must be used and the longer the pulse duration for such laser energy. This increase in energy applied through the epidermis also results in greater absorption of energy by the epidermis.

Therefore, one limitation on the energies which can be used for various dermatological treatments in the dermis, and in particular on the depths in the dermis at which treatments can be performed, is that the energy cannot be so high as to cause damage to the epidermis. One way around this problem, which is for example discussed in U.S. Pat. Nos. 5,057,104 and 5,282,797, issued Oct. 15, 1991 and Feb. 1, 1994, respectively, to Cyrus Chess (the "Chess patents"), is to either place a cold pack in contact with the skin through which laser energy is passed, or to circulate cooling water through an applicator which is in contact with the epidermis. This permits the epidermis to be cooled so as to reduce or possibly eliminate thermal damage to the epidermis while still permitting laser treatment to be performed in the underlying dermal region.

However, these prior art systems have at least two limitations. The first limitation is that it is desirable to have cooling through the entire epidermal layer, which is typically about 0.1 mm thick, since most of the absorption is in the melanin located in the lower portions of the epidermis. However, it is not desirable that the cooling extend significantly below the depth of the epidermis into the dermal layer, cooling at greater depth potentially inhibiting the desired thermal damage to the element in this region. Since a cold pack loses its ability to cool with time, the pack will normally be too cold initially, cooling to too great a depth and, as the pack heats, may not cool to a sufficient depth. The result may thus be to inhibit the desired dermatological treatment while still permitting thermal damage to the epidermis, an undesirable combination. The circulating water embodiment can provide a more even temperature; however, it is still difficult with the circulating water embodiment to assure that cooling for all individuals being treated is to the desired depth, and it is likely that in most instances, the cooling will either be too deep or not deep enough. These techniques also have other limitations, including being cumbersome and relatively expensive to fabricate and/or to use.

The need to control damage to a patient's epidermis means that laser dermatological procedures must now be performed by physicians or other highly trained individuals, and that great care must be exercised in performing such procedures to assure that epidermal damage does not occur without interfering with the desired treatment. It would therefore be preferable if an automatic procedure could be provided to control epidermal temperature through the full depth of the epidermis in the area being treated so as to protect against epidermal damage to a patient while optimizing treatment, thereby permitting laser dermatology procedures to be performed by less highly trained, and therefore less expensive, personnel. However, because of variations in skin pigmentation, differences in epidermal depth and other dermatological differences among patients, such an automatic procedure is difficult to achieve.

A related, but opposite, problem arises in performing certain skin resurfacing/wrinkle removal procedures where the objective is to heat and destroy only the most surface layer(s) of skin with minimal damage to underlying layers. This requires tight control of factors such as laser energy, pulse duration and repetition rate. Again, variations in patient skin means that the procedure can be safely performed only by highly trained and skilled personnel with little margin for error. Similar problems of achieving desired laser treatment while controlling/limiting damage to tissue outside the treatment region arise for other laser medical procedures.

A need therefore exists for an improved method and apparatus for use particularly with laser dermatology systems which automatically protects the patient against damage in skin areas not under treatment, while not interfering with the laser treatment in the skin areas under treatment, thus making such treatments safer and potentially less painful, and permitting the procedures to be performed by less highly trained, and therefore lower cost, personnel.

SUMMARY OF THE INVENTION

In accordance with the above, this invention provides a method and apparatus for use with a system which applies laser energy to selectively treat a selected dermatology problem in a region at or below a patient's skin surface, which method or apparatus optimizes treatment while minimizing damage to the patient's skin areas not under treatment. This objective is achieved by delivering laser energy to the area under treatment, detecting with a suitable sensor at least a selected parameter in a skin region affected by the delivered laser energy, and performing a control function to protect skin not under treatment in the affected region by use of a feedback mechanism which is operative in response to an output from the sensor during the detecting step. More specifically, the laser energy delivered may be controlled by the feedback mechanism to minimize damage to the epidermis through which laser energy is passed to reach a skin area under treatment. Where there is a threshold value for the selected parameter being detected beyond which damage to the epidermis or other untreated skin area may occur, delivery of laser energy may be immediately terminated in response to an indication from the sensor during the detecting step that the threshold value has been reached or exceeded.

For some embodiments of the invention, two laser pulses spaced by a time greater than the thermal relaxation time of the patient's epidermis or other skin area not under treatment which is to be protected, but less than the thermal relaxation time of the skin area under treatment, are delivered for the treatment. The first of the pulses serves as a prediagnosis pulse which is clearly below the damage threshold for a patient's epidermis/protected area. The sensor output during the detecting step for this first pulse is then utilized to control at least one parameter of the second pulse, for example the laser intensity, fluence, and/or duration of such second pulse. The sensor outputs for the second pulse may also be utilized for controlling at least one parameter of such second pulse.

For some embodiments, a mechanism is also provided for controlling the temperature in the epidermis overlying a treatment area under control, at least in part, of a feedback mechanism responsive to outputs from the sensors during the detecting step. The mechanism for controlling temperature may include a mechanism for removing heat from the overlying epidermis, with the feedback mechanism being operative in response to sensor outputs to control the mechanism for removing heat.

For preferred embodiments, the sensor utilized during the detecting step is a temperature sensor, with such temperature sensor being an acoustic sensor for some embodiments, and a spectrum or other optical sensor for other embodiments. An acoustic sensor may also be utilized to provide an indication of epidermal damage or of damage to some other protected skin region. Regardless of the sensor used to detect epidermal damage, a feedback mechanism will operate in response to such an indication to terminate delivery of laser energy. Finally, a cooling spray may be applied to the overlying epidermis, either directly or indirectly in response to an indication from the sensor during the detecting step of actual or potential epidermal damage.

The foregoing and other objects, features and advantages of the invention will be apparent from the following more particular description of preferred embodiments of the invention as illustrated in the accompanying drawings.

IN THE DRAWINGS

FIG. 1 is a schematic semi-block diagram of a simplified laser treatment system in accordance with the teachings of this invention.

Lines A–E of FIG. 2 are waveform diagrams useful in understanding the operation of the system shown in FIG. 1.

DETAILED DESCRIPTION

Figure 1:
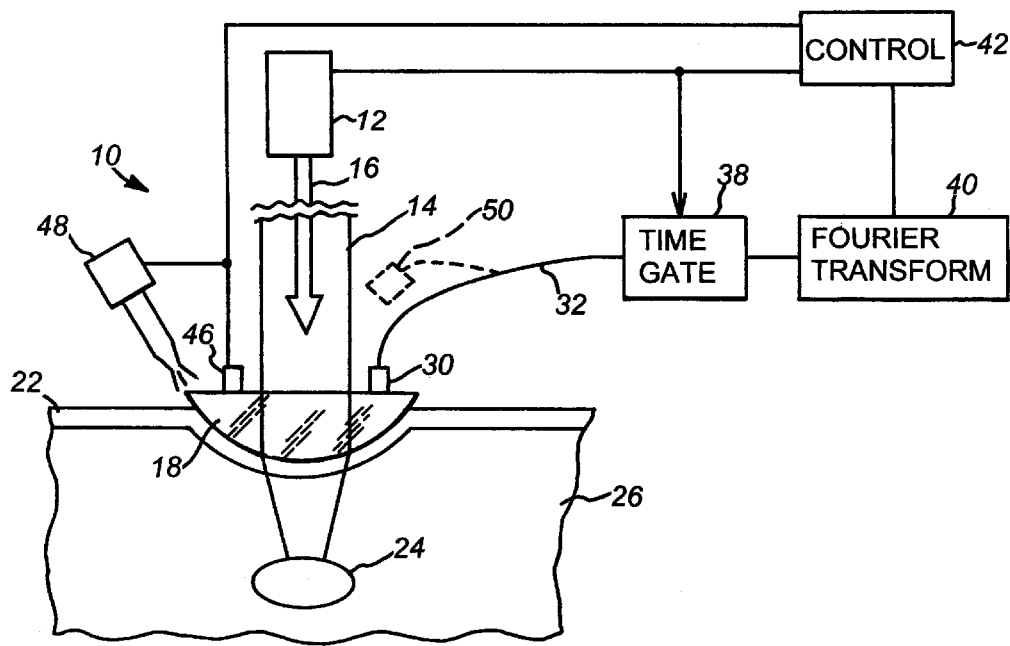

FIG. 1 is a simplified diagram of a laser system 10 which may be utilized for treating a selected dermatological condition. In this system, a laser 12 is utilized to generate a laser signal 14 which may, for example, be applied through an optical fiber 16 and a suitable applicator (not shown) to a lens or other suitable contact element 18 which is in contact with the skin 20 of a patient undergoing treatment. In particular, element 18 is in contact with the epidermal layer 22 of a patient's skin 20 and passes laser beam 14 through epidermal layer 22 to a region 24 in dermal layer 26 of the skin. Region 24 may, for example, contain a hair follicle, or more likely a plurality of hair follicles, which are to be destroyed for removal of unwanted hair, tattoo pigment which is to be removed, veins or other blood vessels visible through the epidermis which are to be coagulated or otherwise destroyed, or other elements which lasers are utilized for the treatment of. Examples of a system of the general type described above utilized for hair removal is described in copending application Ser. No. 08/382,122 filed on behalf of R. Rox Anderson et al. on Feb. 1, 1995 and this application is incorporated herein by reference.

As indicated earlier, one problem with the system described so far is that, since beam 14 can reach region 24 only through epidermis 22, and since epidermis 22 contains melanin and/or other materials absorbing optical energy from the laser beam, the laser beam, in addition to causing potential thermal damage to elements in region 24, also causes heating of epidermis 22 in the area thereof underlying lens 18 through which laser beam 14 passes. However, as the size of elements 24 being treated by laser beam 14 increase, and as the depth of region 24 in which such elements are located increases, the energy of laser beam 14 required to effect treatment, and the duration of the laser pulses required to effect treatment, must also increase. The need to avoid pain to the patient and thermal damage to the patient's epidermis thus becomes a limiting factor on laser dermatological treatments which can be performed. Similar problems arise in other laser dermatology procedures. For example, in skin resurfacing, only a thin surface layer of the skin is to be damaged and removed, with minimal damage to underlying skin areas.

While, as discussed earlier, various techniques have been utilized to cool contact element 18 to remove heat from epidermis 22, thereby reducing or eliminating damage to the epidermis resulting from laser beam 14 passing therethrough, such techniques have been relatively crude and have therefore frequently resulted in either overcooling so as to also cool dermal layer 26, potentially interfering with the treatment in region 24, or in undercooling which may result in thermal damage still occurring in the epidermis 22. FIG. 1 illustrates a technique which permits the temperature of epidermis 22 to be much more closely controlled, permitting differences in skin reaction of various people to be empirically recognized, so that epidermal temperature can be maintained either at a selected temperature or within a selected temperature range which assures cooling through the entire epidermal layer 22 without any significant cooling of dermal layer 26.

Figure 2:
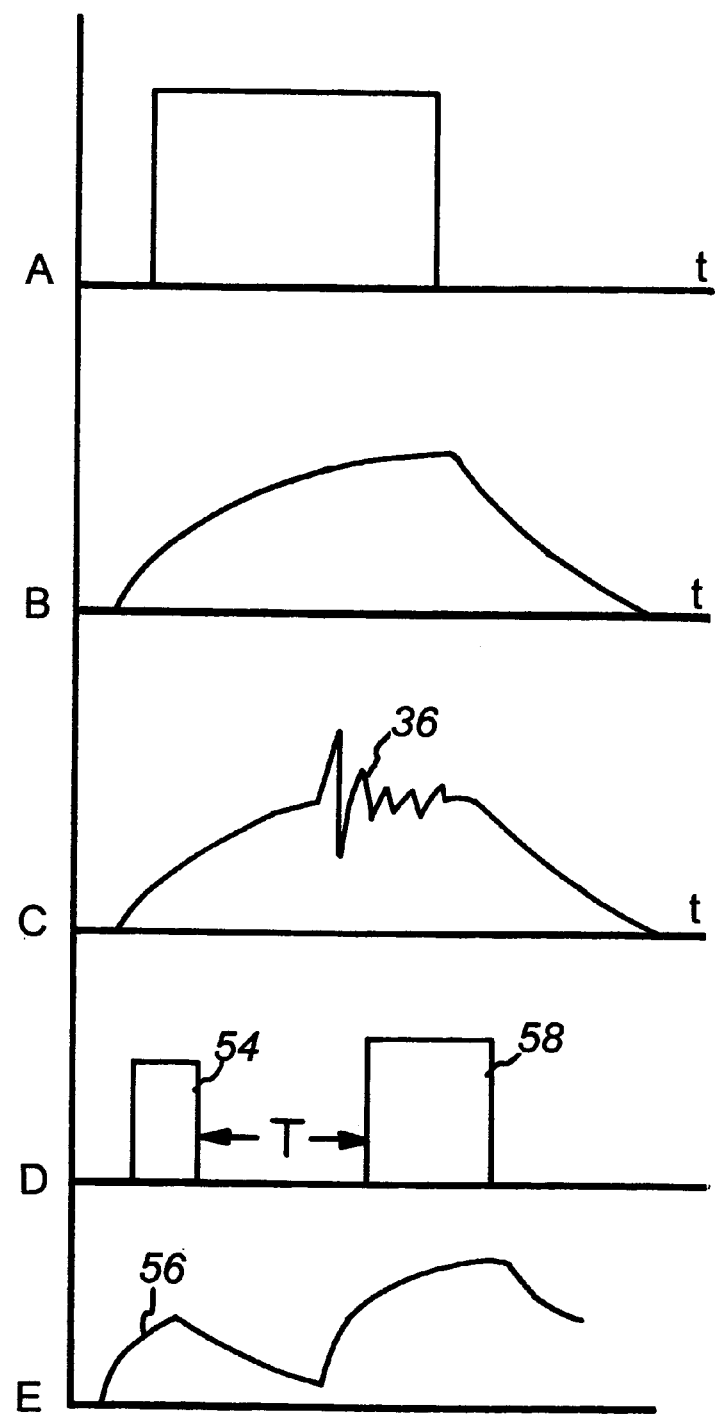

In particular, a temperature sensor 30 is provided in contact with lens 18 which generates an electrical output on line 32 which is indicative of lens temperature. Since lens 18 is in thermal contact with epidermis 22, the temperature of epidermis 22 can be accurately determined from measurements at lens 18. Further, if sensor 30 is an acoustic sensor (for example of a type generally discussed in "Identification of Enamel and Dentine Under Tooth Laser Treatment":, Belikov, Novirov and Scrypnik; Proceedings of Medical Applications of lasers III, Sep. 12–16, 1995, SPIE Vol. 2623, p 109–116), it can be calibrated to operate in a frequency range which picks up audio vibrations from the skin, the amplitude of which varies as a function of temperature. Line A of FIG. 2 illustrates the time duration for a laser pulse 14, and line B of FIG. 2 illustrates the corresponding audio amplitude output from sensor 30 which increases as the temperature of the epidermis increases more or less exponentially with time, and then decreases as the temperature decreases after the laser pulse is terminated. However, if the temperature of the epidermis reaches a point where thermal damage starts to occur, such thermal damage has a unique audio signature which is illustrated on line C of FIG. 2, namely a higher frequency signal 36 superimposed on the normal temperature response. Detection of the higher frequency response 36 can therefore be detected and utilized as an indication that thermal damage is occurring in the skin.

The signal-to-noise ratio for the audio signal on line 32 may be enhanced by utilizing a time gate 38 which is synchronized to the operation of laser 12, and by utilizing a Fourier transform circuit 40 as a frequency gate to filter out signals other than the desired audio output. The desired audio signal is typically the 1 Kz to 1 meg range. The output from Fourier transform circuit 40 is applied to a control processor 42. For some embodiments of the invention, the time gate function 38 and the Fourier transform function 40 may also be performed in the control processor 42.

Control processor 42 may utilize the temperature indication from sensor 30 in a number of ways. First, control 42 may apply a signal to laser 12, not only to turn the laser on and to turn the laser off, but also to control the intensity, fluence, and/or pulse duration for laser 12 based on the temperature readings from sensor 30. Thus, if it is detected that the temperature in epidermis 22 is rising too rapidly, the laser fluence may be slightly reduced to prevent overheating of the epidermis. Conversely, if the epidermis is not heating as rapidly as anticipated, it may be possible to increase the fluence of laser 14 so as to improve the effectiveness of the treatment being performed. Further, if at any time a pattern 36 is detected by control 42 from detector 30, a signal can be applied to laser 12 (or removed from the laser) to immediately terminate operation of the laser, thus minimizing the damage being caused.

FIG. 1 illustrates two additional options for use of the temperature indications from sensor 30 by control 42. First, various techniques are available for cooling lens 18 including passing circulating water therethrough as previously discussed. One such technique is to have an thermoelectric component 46 in thermal contact with lens 18, the cool side of component 46 drawing heat from epidermis 22 through lens 18. This technique for cooling the lens is discussed in greater detail in co-pending application Ser. No. 08/759.135, filed Dec. 2, 1996 in the name of Gregory Altshuler and assigned to the assignee of the current application, the description in this co-pending application being incorporated herein by reference. Since the amount of heat withdrawn from the epidermis by a thermoelectric device 46 is proportional to the current flowing through such device, control 42 may operate in response to the temperature detected by sensor 30 to either increase or decrease the current flow through device 46 to maintain epidermis 22 at a desired temperature. The water temperature or flow rate may also be controlled, where flowing water is used to cool lens 18, to maintain epidermis 22 at a desired temperature. However, one problem with this approach is that the response time to change temperature with a thermoelectric device 46 is in the tens of milliseconds to seconds range, while the response time with flowing water is substantially greater. Therefore, while these techniques can be utilized to supplement other controls on temperature, in most instances they will not be sufficient alone to maintain epidermis 22 within a desired temperature range.

It is also possible, depending on the element being treated in region 24 that there will be a unique acoustic output when destruction of the element has occurred. For example, when a hair follicle is destroyed or when blood coagulates in a vein or other blood vessel under treatment, this change will generate an audio signature which may, with suitable programming be detected to indicate when the desired treatment has been completed. The detection that the desired treatment has been completed can be utilized by control 42 to turn off laser 12. This assures that the epidermis is exposed to no more laser radiation than is necessary to achieve the desired treatment and thus further protects the epidermis against damage without sacrificing effective treatment.

Another option when an overheating condition is detected is to utilize a device 48 to spray a cooling liquid or a cooling gas on lens 18 and/or on epidermis 22 to effect rapid cooling. This is particularly desirable in a situation where thermal damage profile 36 has been detected and laser 12 cut off, the spray rapidly cooling the epidermis to minimize the thermal damage. Equipment 48 is currently available to permit such a spray to be generated in 1 to 1K ms. An example of such equipment is also discussed in the beforementioned SPIE publication.

While in FIG. 1 acoustic detector 30 has been shown as being in contact with lens 18, and picking up vibrations in the audio range through this transducer, such audio signals could also be picked up by a microphone 50 suitably positioned at a short distance from lens 18. A suitable distance for microphone 50 from lens 18 and/or from epidermis 22 would be approximately zero to two inches.

The system of FIG. 1 could also operate in a different mode which is illustrated by lines D and E of FIG. 2. Referring to line D, laser 12 puts out a first pulse 54 which is sufficiently low in energy and duration so as to be well below the damage threshold for epidermis 22. Sensor 30 detects the temperature rise 56 (line E) caused by pulse 54 and transmits this information to control 42 where this information is utilized to determine the temperature response of the patient's epidermis. A second laser pulse 58 is then applied which pulse is of an intensity and duration determined by the control so as to be adequate to achieve the desired dermatological treatment of the element in region 24 without causing thermal damage to the patient's epidermis. The time between pulses 54 and 58 is less than the thermal relaxation time in dermis 26 so that the heat produced by pulse 54 is still present in region 24. However, fortuitously, the thermal relaxation time in epidermis 22 is less than that in dermis 26 so that, as indicated by line E, much of the heat caused by pulse 54 has left epidermal region 22 before the second pulse 58 is applied. Thus, the two pulses have a cumulative effect in region 24, while not having a cumulative effect in epidermis 22, thus permitting the desired thermal effect on the element being treated in region 24 without damaging epidermis 22, the parameters for pulse 58 being carefully selected to achieve this objective. Further, the success of the calculations in determining the parameters for pulse 58 can be verified by using sensor 30 to monitor the temperature/condition of epidermis 22 during pulse 58 and performing one or more of the control functions previously discussed to protect against epidermal damage if the temperature detector indicates that such action is required.

Figure 3:
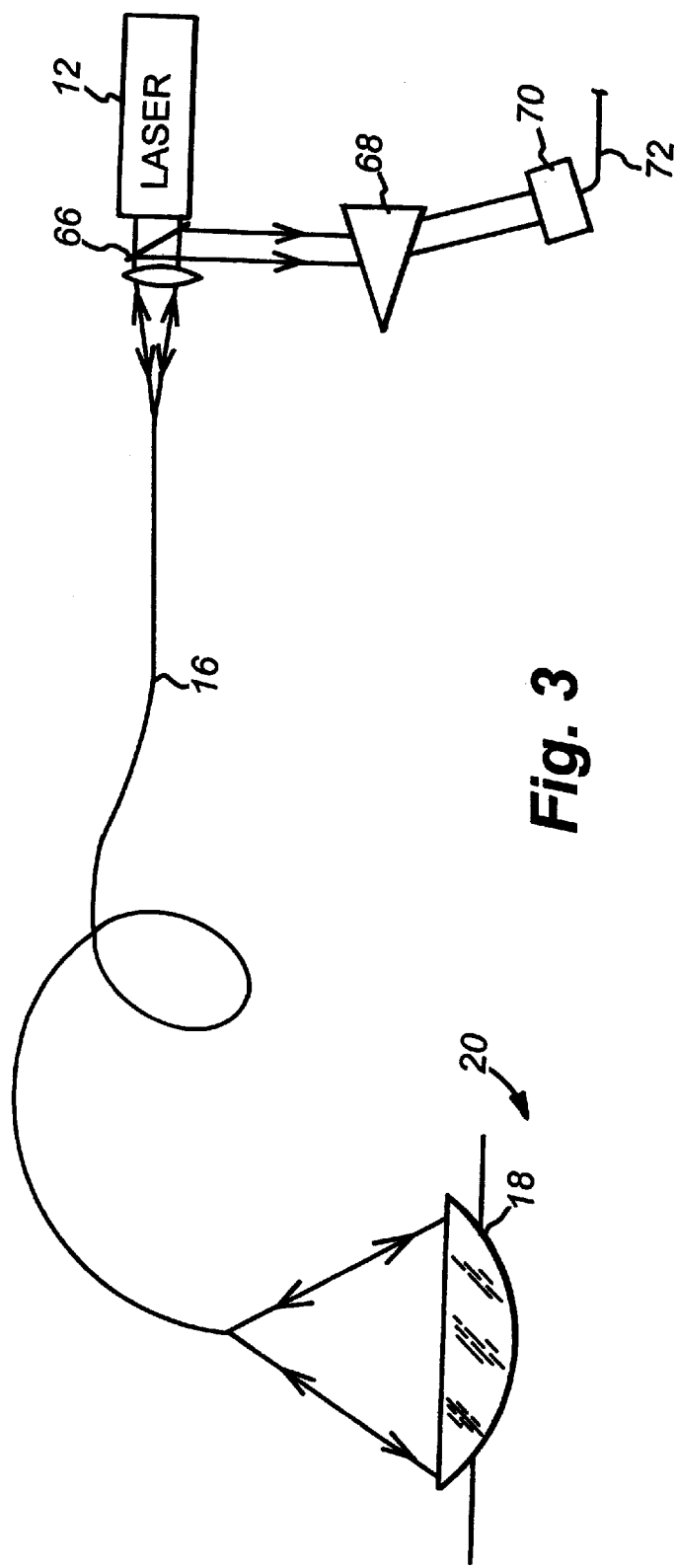
FIG. 3 is a simplified schematic diagram for an alternative embodiment of the invention.
Figure 4:
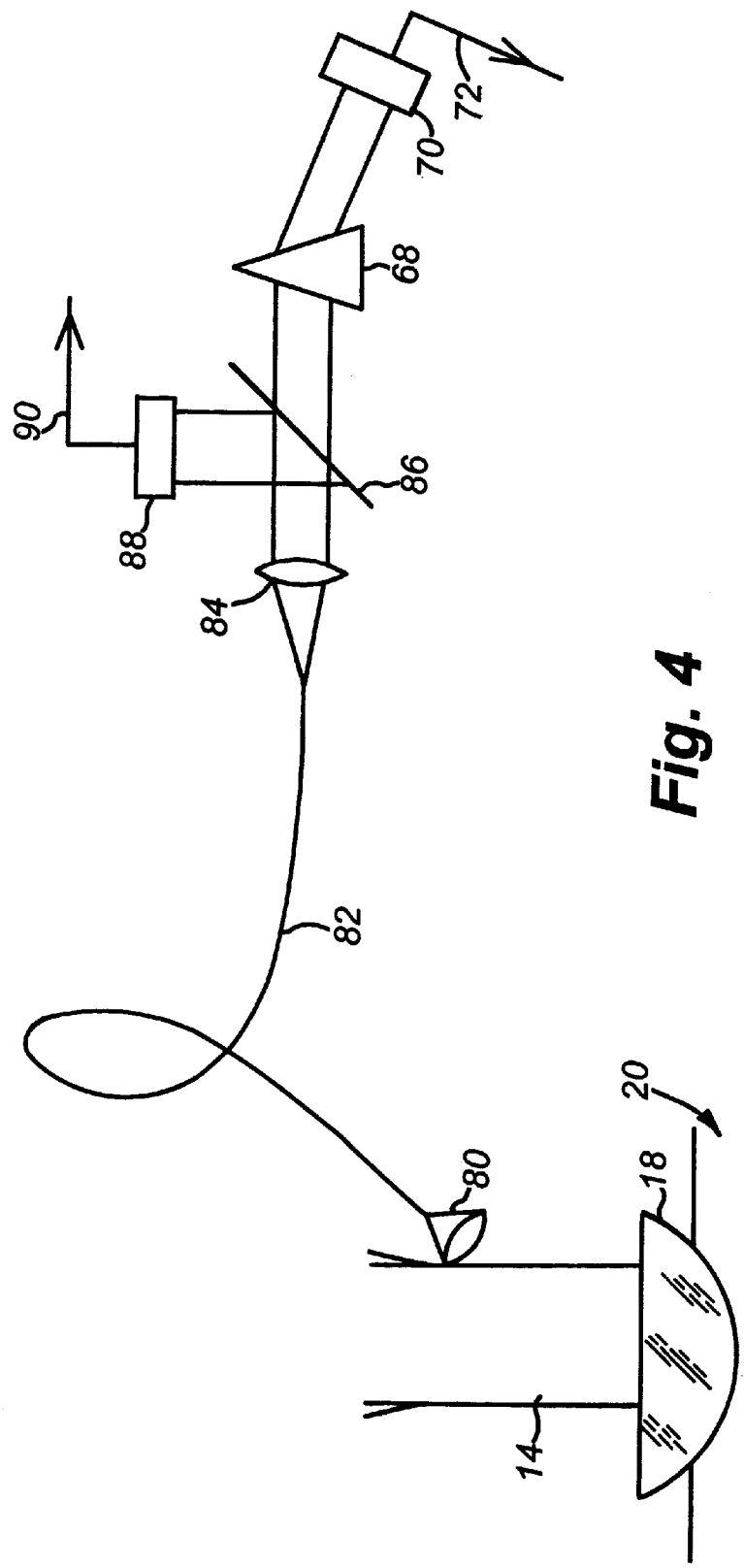
FIG. 4 is a simplified schematic diagram for still another alternative embodiment of the invention.

FIGS. 3 and 4 illustrate embodiments of the invention wherein optical temperature sensing is utilized rather than acoustic sensing. In FIG. 3, the pulse from laser 12 is applied to lens 18 through optical fiber 16 and a suitable applicator. Light reflected from the surface of epidermis 22 is transmitted back through lens 18 to fiber 16 and through fiber 16 and beam splitter 66 to spectrometer 68 and detector 70. Detector 70 may detect only a selected one or more regions of the light output from spectrometer 68, for example the infrared light, or may detect light across the full spectrum outputted from the spectrometer. The output from detector 20, which is indicative of temperature at the surface of epidermis 22 and, depending on color, may also be indicative of thermal damage occurring, is applied from detector 70 through a line 72 to a suitable control such as control 42, which operates to control laser 12, and where appropriate various cooling elements, in the manner previously described.

FIG. 4 differs from FIG. 3 in two respects. First, rather than using the same fiber 16 to both apply laser energy and to optically detect radiation from skin 20, a separate optical detector 80 is provided to receive optical energy reflected back through lens 18. Optical energy received by detector 80 is passed through a separate optical fiber 82 to a lens or other suitable optical output element 84. The output from element 84 is applied to a beam splitter 86 which passes part of the light to an infrared detector 88 and the remainder of the light through a spectrometer 68 and detector 70 to an output 72. The output from infrared detector 88 is applied through a line 90 to, for example, control 42.

The signal from infrared detector 88 may be utilized to provide an indication of epidermis or surface temperature while the output from detector 70 may for example provide an indication of skin color which, in addition to serving as an indication of temperature, may also provide an indication of actual or potential thermal damage to the epidermis. Detector 70 may also be utilized to monitor the color of, for example, a vein being treated or a tattoo pigment being removed, the output from detector 70 indicating when the color of the vein changes to indicate coagulation therein or when the color of the tattoo pigment changes indicating destruction thereof. As discussed earlier, such indication may be utilized to empirically terminate treatment by turning off laser 12, thereby assuring that epidermis 22 is not exposed to any more laser radiation than is absolutely necessary.

While acoustic and optical temperature sensors have been utilized for the preferred embodiments discussed above, it is apparent that other temperature sensors known in the art, for example thermoelectric detectors such as thermocouples, might be utilized for performing temperature measurement in suitable applications. Further, while temperature and/or initial damage to the epidermis or destruction of the desired element in region 24 have been utilized as the detected condition or perameter for control to prevent epidermal damage and to assure that the desired treatment has been effected, other parameters may be measured and utilized to control laser energy, duration and/or epidermal cooling in suitable applications. In addition, while several methods of cooling the skin have been discussed above, other cooling techniques may be utilized for some applications. Further, while specific configurations have been shown, for example, with a lens 18 in contact with the skin, for the preferred embodiments, this is not a limitation on the invention, and the invention may be practiced with other laser dermatological systems which, for example, do not utilize a lens in contact with the skin to apply the laser and, which, in fact, do not have a contact element at all. Finally, while the preferred embodiments involve specific laser dermatology treatments, the invention may also be utilized to monitor and control other laser dermatology treatments to minimize damage to skin areas outside the treatment region. The invention generally requires only that a selected perameter of the skin undergoing treatment be detected and that this detection be utilized to control the treatment. Thus, while the invention has been particularly shown and described above, with reference to preferred embodiments, the foregoing and other changes in form and detail may be made therein by one skilled in the art, and the invention is to be defined only by the following claims.

What is claimed is:

1. In a system for using a laser to treat a selected problem in a region at a selected depth in a patient's skin, a mechanism for reducing damage to the patient's epidermis overlying such region comprising:

a sensor for detecting at least a selected parameter of the patient's skin;

a feedback mechanism operative in response to an output from said sensor for performing a control function which protects said overlying epidermis from damage; and means for delivering two laser pulses to said region through said overlying epidermis, said pulses being spaced by a time related at least to the thermal relaxation time of the patient's epidermis, the first of said pulses being a prediagnosis pulse which is below a damage threshold for the patient's epidermis, the feedback mechanism being operative in response to the sensor output for said first pulse for controlling at least one parameter of the second pulse.

2. A mechanism as claimed in claim 1, wherein the at least one parameter controlled includes at least one of laser intensity, fluence and pulse duration.

3. A mechanism as claimed in claim 1, wherein said feedback mechanism is operative in response to sensor outputs for said second pulse for controlling at least one parameter of said second pulse.

4. In a system for using a laser to treat a selected problem in a region at a selected depth in a patient's skin, a method for reducing damage to the patient's epidermis overlying such region comprising:

detecting at least a selected parameter of the patient's skin;

performing a control function to protect said overlying epidermis from damage in response to an output from said sensor; and delivering two laser pulses to said region through said overlying epidermis, which pulses are spaced by a time related at least to the thermal relaxation time of the patient's epidermis, the first of said pulses being a prediagnosis pulse which is below a damage threshold for the patient's epidermis, the control function utilizing the detected at least selected parameter for said first pulse to control at least one parameter of the second pulse.

5. A method as claimed in claim 4, wherein the control function includes controlling the laser energy delivered to said region by said second pulse so as to minimize potential epidermal damage.

6. A method as claimed in claim 4, wherein the at least one parameter controlled includes at least one of laser intensity, fluence and pulse duration.

7. A method as claimed in claim 4, wherein said control function is also operative in response to a selected parameter detected during said detecting step for said second pulse for controlling at least one parameter of said second pulse.

8. A method as claimed in claim 4, including the step of applying a cooling spray to said overlying epidermis, said step being in response to an indication during said detecting step of potential epidermal damage.

9. A method as claimed in claim 4, wherein during said detection step for said second pulse, an indication that treatment of the problem is complete is detected, and wherein said control function terminates delivery of laser energy in response to a treatment complete indication.

* * * * *